United States Patent [19]
Murphy et al.

[11] Patent Number: 6,136,583
[45] Date of Patent: *Oct. 24, 2000

[54] AMIDASE

[75] Inventors: Dennis Murphy, Paoli; John Reid, Bryn Mawr, both of Pa.; Dan Robertson, Haddonfield, N.J.

[73] Assignee: Diversa Corporation, San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/951,088

[22] Filed: Oct. 15, 1997

Related U.S. Application Data

[62] Division of application No. 08/664,646, Jun. 17, 1996, Pat. No. 5,877,001.

[51] Int. Cl.[7] ............... C12N 9/78; C12N 9/80; C12N 1/20; C07H 21/04
[52] U.S. Cl. ............ 435/227; 435/228; 435/230; 435/69.1; 435/252.3; 435/320.1; 530/350; 536/23.2; 536/23.7
[58] Field of Search ................... 435/227, 228, 435/69.1, 252.3, 320.1; 530/350; 536/23.2, 23.7

[56] References Cited

U.S. PATENT DOCUMENTS

| | | | |
|---|---|---|---|
| 5,190,875 | 3/1993 | Steinke et al. | 435/227 |
| 5,451,522 | 9/1995 | Queener et al. | 435/252.3 |
| 5,494,796 | 2/1996 | Spears et al. | 435/6 |

*Primary Examiner*—Ponnathapu Achutamurthy
*Assistant Examiner*—Tekchand Saidha
*Attorney, Agent, or Firm*—Gray Cary Ware & Freidenrich LLP; Lisa A. Haile

[57] ABSTRACT

A purified thermostable enzyme is derived from the archael bacterium Thermococcus GU5L5. The enzyme has a molecular weight of about 68.5 kilodaltons and has cellulase activity. The enzyme can be produced from native or recombinant host cells and can be used for the removal of arginine, phenylalanine, or methionine amino acids from the N-terminal end of peptides in peptide or peptidomimetic synthesis. The enzyme is selective for the L, or 'natural' enantiomer of the amino acid derivatives and is therefore useful for the production of optically active compounds. These reactions can be performed in the presence of the chemically more reactive ester functionality, a step which is very difficult to achieve with nonenzymatic methods.

5 Claims, 6 Drawing Sheets

Thermococcus GU5L5 Amidase

```
  1  ATG ACC GGC ATC GAA TGG AAC CAC GAG ACC TTT TCT AAG TTC GCC TAC CTG GGC GAC CCG   60
  1  Met Thr Gly Ile Glu Trp Asn His Glu Thr Phe Ser Lys Phe Ala Tyr Leu Gly Asp Pro   20

61  AGG ATA CGG GGA AAC TTA ATC GCG TAC ACC CTG ACG AAG GCC AAC ATG AAG GAC AAC AAG
 21  Arg Ile Arg Gly Asn Leu Ile Ala Tyr Thr Leu Thr Lys Ala Asn Met Lys Asp Asn Lys   40

121  TAC GAG AGC ACG GTT GTT GTT GAA GAC CTT GAA ACG GGC TCA AGG CGC TTC ATC GAG AAC  180
 41  Tyr Glu Ser Thr Val Val Val Glu Asp Leu Glu Thr Gly Ser Arg Arg Phe Ile Glu Asn   60

181  GCC TCA ATG CCG AGG ATT TCG CCA GAC GGC AGA AAG CTC GCC TTC ACC TGC TTT AAC GAG  240
 61  Ala Ser Met Pro Arg Ile Ser Pro Asp Gly Arg Lys Leu Ala Phe Thr Cys Phe Asn Glu   80

241  GAG AAG AAG GAG ACC GAG ATA TGG GTG GCC GAT ATC CAG ACC CTG AGC GCC AAG AAA GTC
 81  Glu Lys Lys Glu Thr Glu Ile Trp Val Ala Asp Ile Gln Thr Leu Ser Ala Lys Lys Val  100
                                                                                      300
```

FIG. 1A

301 CTC TCA ACT AAA AAC GTC CGC TCG ATG CAG TGG AAC GAC GAT TCA AGG AGA CTC TTA GTT 360
101 Leu Ser Thr Lys Asn Val Arg Ser Met Gln Trp Asn Asp Asp Ser Arg Arg Leu Leu Val 120

361 GTC GGC TTC AAG AGG AGG GAC TTC GTC TTT GAC GAC GTC CCG GTC TGG 420
121 Val Gly Phe Lys Arg Arg Asp Phe Val Phe Asp Asp Val Pro Val Trp 140

421 TTC GAC AAT ATG GGA TTC TTT GAT GGA GAG AAG ACG ACG TTC TGG GTT CTT GAC ACT GAG 480
141 Phe Asp Asn Met Gly Phe Phe Asp Gly Glu Lys Thr Thr Phe Trp Val Leu Asp Thr Glu 160

481 GCC GAG GAG ATA ATC GAG CAG TTC GAG AAG CCG AGG TTT TCG AGT GGC CTC TGG CAC GGC 540
161 Ala Glu Glu Ile Ile Glu Gln Phe Glu Lys Pro Arg Phe Ser Ser Gly Leu Trp His Gly 180

541 GAT GCG ATA GTT GTG AAC GTC CCG CAC CGC GAG GGG AGC AAG CCT GCC CTG TTC AAG TTC 600
181 Asp Ala Ile Val Val Asn Val Pro His Arg Glu Gly Ser Lys Pro Ala Leu Phe Lys Phe 200

601 TAC GAC ATA GTC CTA TGG AAG GAC GGG GAG GAA GAG AAG CTC TTC GAG AGG GTC TCC TTC 660
201 Tyr Asp Ile Val Leu Trp Lys Asp Gly Glu Glu Lys Leu Phe Glu Arg Val Ser Phe 220

661 GAG GCG GTT GAC TCC GAC GGA AAG AGA ATA CTC CTG AGG GGC AAG AAA AAA AAG CGG TTC 720
221 Glu Ala Val Asp Ser Asp Gly Lys Arg Ile Leu Leu Arg Gly Lys Lys Lys Lys Arg Phe 240

FIG. 1B

721 ATC AGC GAG CAC GAC TGG CTG TAC CTC TGG GAC GGC GAG CTT AAA CCG ATC TAC GAG GGC   780
241 Ile Ser Glu His Asp Trp Leu Tyr Leu Trp Asp Gly Glu Leu Lys Pro Ile Tyr Glu Gly   260

781 CCG CTC GAC GTC TGG GAA GCC AAG CTC ACG GAA GGA AAG GTC TAC TTC CTC ACT CCA GAT   840
261 Pro Leu Asp Val Trp Glu Ala Lys Leu Thr Glu Gly Lys Val Tyr Phe Leu Thr Pro Asp   280

841 GCG GGC AGG GTA AAC CTC TGG CTC TGG GAC GGG AAG GCC GAG CGT GTT ACC GGC GAC   900
281 Ala Gly Arg Val Asn Leu Trp Leu Trp Asp Gly Lys Ala Glu Arg Val Val Thr Gly Asp   300

901 CAC TGG ATT TAC GGG CTT GAC GTC AGC GAT GGC AAA GCA TTG CTC CTC ATC ATG ACC GCC   960
301 His Trp Ile Tyr Gly Leu Asp Val Ser Asp Gly Lys Ala Leu Leu Leu Ile Met Thr Ala   320

961 ACG AGG ATA GGC GAG CTC TAC CTC TAC GAC GGC GAG CTG AAA CAG GTC ACC GAA TAC AAC
1020
321 Thr Arg Ile Gly Glu Leu Tyr Leu Tyr Asp Gly Glu Leu Lys Gln Val Thr Glu Tyr Asn   340

1021 GGG CCG ATA TTC AGG AAG CTC AAG ACC TTC GAG CCG AGG CAC TTC CGC TTC AAG AGC AAA
1080
341 Gly Pro Ile Phe Arg Lys Leu Lys Thr Phe Glu Pro Arg His Phe Arg Phe Lys Ser Lys   360

1081 GAC CTC GAG ATA GAC GGC TGG TAC CTC AGG CCG GAG GTT AAA GAG GAG AAG GCC CCG GTG
1140
361 Asp Leu Glu Ile Asp Gly Trp Tyr Leu Arg Pro Glu Val Lys Glu Glu Lys Ala Pro Val   380

FIG. 1C

1141 ATA GTC TTC GTC CAC GGC GGG CCG AAG GGC ATG TAC GGA CAC CGC TTC GTC TAC GAG ATG
1200
381  Ile Val Phe Val His Gly Gly Pro Lys Gly Met Tyr Gly His Arg Phe Val Tyr Glu Met  400

1201 CAG CTG ATG GCG AGC AAG GGC TAC TAC GTC GTC TTC GTG AAC CCG CGC GGC AGC GAC GGC
1260
401  Gln Leu Met Ala Ser Lys Gly Tyr Tyr Val Val Phe Val Asn Pro Arg Gly Ser Asp Gly  420

1261 TAT AGC GAA GAC TTC GCG CTC CGC GTC CTG GAG AGG ACT GGC TTG GAG GAC TTT GAG GAC
1320
421  Tyr Ser Glu Asp Phe Ala Leu Arg Val Leu Glu Arg Thr Gly Leu Glu Asp Phe Glu Asp  440

1321 ATA ATG AAC GGC ATC GAG GAG TTC TTC AAG CTC GAA CCG CAG GCC GAC AGG GAG CGC GTT
1380
441  Ile Met Asn Gly Ile Glu Glu Phe Phe Lys Leu Glu Pro Gln Ala Asp Arg Glu Arg Val  460

1381 GGA ATA ACG GGC ATA AGC TAC GGC GGC TTC ATG ACC AAC TGG GCC TTG ACT CAG AGC GAC
1440
461  Gly Ile Thr Gly Ile Ser Tyr Gly Gly Phe Met Thr Asn Trp Ala Leu Thr Gln Ser Asp  480

1441 CTC TTC AAG GCA GGA ATA AGC GAG AAC GGC ATA AGC TAC TGG CTC ACC AGC TAC GCC TTC
1500
481  Leu Phe Lys Ala Gly Ile Ser Glu Asn Gly Ile Ser Tyr Trp Leu Thr Ser Tyr Ala Phe  500

```
1501  TCG GAC ATA GGG CTC TGG TAC GAC GTC GAG GTC ATC GGG CCA AAT CCG TTA GAG AAC GAG  1560
 501  Ser Asp Ile Gly Leu Trp Tyr Asp Val Glu Val Ile Gly Pro Asn Pro Leu Glu Asn Glu  520

1561  AAC TTC AGG AAG CTC AGC CCG CTG TTC TAC GCT CAG AAC GTG AAG GCG CCG ATA CTC CTA  1620
 521  Asn Phe Arg Lys Leu Ser Pro Leu Phe Tyr Ala Gln Asn Val Lys Ala Pro Ile Leu Leu  540

1621  ATC CAC TCG CTT GAG GAC TAC CGC TGT CCG CTC GAC CAG AGC CTT ATG TTC TAC AAC GTG  1680
 541  Ile His Ser Leu Glu Asp Tyr Arg Cys Pro Leu Asp Gln Ser Leu Met Phe Tyr Asn Val  560

1681  CTC AAG GAC ATG GGC AAG GAA GCC TAC ATA GCG ATA TTC AAG CGC GGC GCC CAC GGC CAC  1740
 561  Leu Lys Asp Met Gly Lys Glu Ala Tyr Ile Ala Ile Phe Lys Arg Gly Ala His Gly His  580

1741  AGC GTC CGC GGA AGC CCG AGG CAC AGG CCG AAG CGC TAC AGG CTC TTC ATA GAG TTC TTC  1800
 581  Ser Val Arg Gly Ser Pro Arg His Arg Pro Lys Arg Tyr Arg Leu Phe Ile Glu Phe Phe  600

1801  GAG CGC AAG CTC AAG AAG TAC GAG GAG GGC TTT GAG GTA GAG AAG ATA CTC AAG GGG AAT  1860
 601  Glu Arg Lys Leu Lys Lys Tyr Glu Glu Gly Phe Glu Val Glu Lys Ile Leu Lys Gly Asn  620

1861  GGG AAC TGA  1869
 621  Gly Asn End  623
```

AMIDASE

This is a divisional of application Ser. No. 08/664,646, filed Jun. 17, 1996 now U.S. Pat. No. 5,877,001.

This invention relates to newly identified polynucleotides, polypeptides encoded by such polynucleotides, the use of such polynucleotides and polypeptides, as well as the production and isolation of such polynucleotides and polypeptides. More particularly, the polypeptide of the present invention has been identified as an amidase and in particular an enzyme having activity in the removal of arginine, phenylalanine or methionine from the N-terminal end of peptides in peptide or peptidomimetic synthesis.

Thermophilic bacteria have received considerable attention as sources of highly active and thermostable enzymes (Bronneomeier, K. and Staudenbauer, W. L., D. R. Woods (Ed.), The Clostridia and Biotechnology, Butterworth Publishers, Stoneham, Mass. (1993). Recently, the most extremely thermophilic organotrophic eubacteria presently known have been isolated and characterized. These bacteria, which belong to the genus Thermotoga, are fermentative microorganisms metabolizing a variety of carbohydrates (Huber, R. and Stetter, K. O., in Ballows, et al., (Ed.), The Procaryotes, 2nd Ed., Springer-Verlaz, New York, pgs. 3809–3819 (1992)).

Because to date most organisms identified from the archaeal domain are thermophiles or hyperthermophiles, archaeal bacteria are also considered a fertile source of thermophilic enzymes.

In accordance with one aspect of the present invention, there is provided a novel enzyme, as well as active fragments, analogs and derivatives thereof.

In accordance with another aspect of the present invention, there are provided isolated nucleic acid molecules encoding an enzyme of the present invention including mRNAs, DNAs, cDNAs, genomic DNAs as well as active analogs and fragments of such enzymes.

In accordance with yet a further aspect of the present invention, there is provided a process for producing such polypeptide by recombinant techniques comprising culturing recombinant prokaryotic and/or eukaryotic host cells, containing a nucleic acid sequence encoding an enzyme of the present invention, under conditions promoting expression of said enzyme and subsequent recovery of said enzyme.

In accordance with yet a further aspect of the present invention, there is provided a process for utilizing such enzyme, or polynucleotide encoding such enzyme. The enzyme is useful for the removal of arginine, phenylalanine, or methionine amino acids from the N-terminal end of peptides in peptide or peptidomimetic synthesis. The enzyme is selective for the L, or "natural" enantiomer of the amino acid derivatives and is therefore useful for the production of optically active compounds. These reactions can be performed in the presence of the chemically more reactive ester functionality, a step which is very difficult to achieve with nonenzymatic methods. The enzyme is also able to tolerate high temperatures (at least 70° C.), and high concentrations of organic solvents (>40% DMSO), both of which cause a disruption of secondary structure in peptides; this enables cleavage of otherwise resistant bonds.

In accordance with yet a further aspect of the present invention, there is also provided nucleic acid probes comprising nucleic acid molecules of sufficient length to specifically hybridize to a nucleic acid sequence of the present invention.

In accordance with yet a further aspect of the present invention, there is provided a process for utilizing such enzymes, or polynucleotides encoding such enzymes, for in vitro purposes related to scientific research, for example, to generate probes for identifying similar sequences which might encode similar enzymes from other organisms.

These and other aspects of the present invention should be apparent to those skilled in the art from the teachings herein.

The following drawings are illustrative of embodiments of the invention and are not meant to limit the scope of the invention as encompassed by the claims.

FIGS. 1A–1E are an illustration of the full-length DNA and corresponding deduced amino acid sequence of the enzyme of the present invention. Sequencing was performed using a 378 automated DNA sequencer (Applied Biosystems, Inc.).

Figure 2:
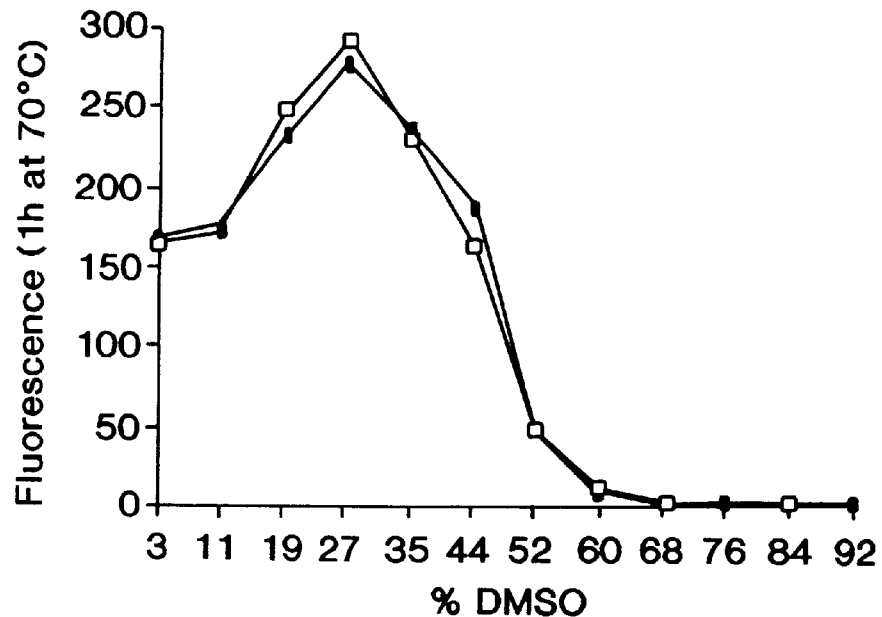
FIG. 2 shows the fluorescence versus concentration of DMSO. The filled and open boxes represent individual assays from Example 3.

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The present invention provides a purified thermostable enzyme that catalyzes the removal of arginine, phenylalanine, or methionine amino acids from the N-terminal end of peptides in peptide or peptidomimetic synthesis. The purified enzyme is an amidase derived from an organism referred to herein as "Thermococcus GU5L5"

which is a thermophilic archaeal organism which has a very high temperature optimum. The organism is strictly anaerobic and grows between 55 and 90° C. (optimally at 85° C.). GU5L5 was discovered in a shallow marine hydrothermal area in Vulcano, Italy. The organism has coccoid cells occurring in singlets or pairs. GU5L5 grows optimally at 85° C. and pH 6.0 in a marine medium with peptone as a substrate and nitrogen in gas phase.

The polynucleotide of this invention was originally recovered from a genomic gene library derived from Thermococcus GU5L5 as described below. It contains an open reading frame encoding a protein of 622 amino acid residues.

In a preferred embodiment, the amidase enzyme of the present invention has a molecular weight of about 68.5 kilodaltons as inferred from the nucleotide sequence of the gene.

In accordance with an aspect of the present invention, there are provided isolated nucleic acid molecules (polynucleotides) which encode for the mature enzyme having the deduced amino acid sequence of FIG. 1 (SEQ ID NO:2).

This invention, in addition to the isolated nucleic acid molecule encoding an amidase enzyme disclosed in FIG. 1 (SEQ ID NO:1), also provides substantially similar sequences. Isolated nucleic acid sequences are substantially similar if: (i) they are capable of hybridizing under stringent conditions, hereinafter described, to SEQ ID NO:1; or (ii) they encode DNA sequences which are degenerate to SEQ ID NO:1. Degenerate DNA sequences encode the amino acid sequence of SEQ ID NO:2, but have variations in the nucleotide coding sequences. As used herein, "substantially similar" refers to the sequences having similar identity to the sequences of the instant invention. The nucleotide sequences that are substantially similar can be identified by hybridization or by sequence comparison. Enzyme sequences that are substantially similar can be identified by one or more of the following: proteolytic digestion, gel electrophoresis and/or microsequencing.

One means for isolating a nucleic acid molecule encoding an amidase enzyme is to probe a gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated to one skilled in the art that SEQ ID NO:1, or fragments thereof (comprising at least 15 contiguous nucleotides), is a particularly useful probe. Other particular useful probes for this purpose are hybridizable fragments to the sequences of SEQ ID NO:1 (i.e., comprising at least 15 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acid is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/mL polyriboadenylic acid. Approximately $2 \times 10^7$ cpm (specific activity $4-9 \times 10^8$ cpm/ug) of $^{32}P$ end-labeled oligonucleotide probe are then added to the solution. After 12–16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at Tm-10° C. for the oligo-nucleotide probe. The membrane is then exposed to auto-radiographic film for detection of hybridization signals.

Stringent conditions means hybridization will occur only if there is at least 90% identity, preferably at least 95% identity and most preferably at least 97% identity between the sequences. See J. Sambrook et al., Molecular Cloning, A Laboratory Manual (2d Ed. 1989) (Cold Spring Harbor Laboratory) which is hereby incorporated by reference in its entirety.

"Identity" as the term is used herein, refers to a polynucleotide sequence which comprises a percentage of the same bases as a reference polynucleotide (SEQ ID NO:1). For example, a polynucleotide which is at least 90% identical to a reference polynucleotide, has polynucleotide bases which are identical in 90% of the bases which make up the reference polynucleotide and may have different bases in 10% of the bases which comprise that polynucleotide sequence.

The present invention also relates to polynucleotides which differ from the reference polynucleotide such that the changes are silent changes, for example the changes do not alter the amino acid sequence encoded by the polynucleotide. The present invention also relates to nucleotide changes which result in amino acid substitutions, additions, deletions, fusions and truncations in the enzyme encoded by the reference polynucleotide (SEQ ID NO:1). In a preferred aspect of the invention these enzymes retain the same biological action as the enzyme encoded by the reference polynucleotide.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other animal sources or to screen such sources for related sequences.

The coding sequence for the amidase enzyme of the present invention was identified by preparing a Thermococcus GU5L5 genomic DNA library and screening the library for the clones having amidase activity. Such methods for constructing a genomic gene library are well-known in the art. One means, for example, comprises shearing DNA isolated from GU5L5 by physical disruption. A small amount of the sheared DNA is checked on an agarose gel to verify that the majority of the DNA is in the desired size range (approximately 3–6 kb). The DNA is then blunt ended using Mung Bean Nuclease, incubated at 37° C. and phenol/chloroform extracted. The DNA is then methylated using Eco RI Methylase. Eco R1 linkers are then ligated to the blunt ends through the use of T4 DNA ligase and incubation at 4° C. The ligation reaction is then terminated and the DNA is cut-back with Eco R1 restriction enzyme. The DNA is then size fractionated on a sucrose gradient following procedures known in the art, for example, Maniatis, T., et al., Molecular Cloning, Cold Spring Harbor Press, New York, 1982, which is hereby incorporated by reference in its entirety.

A plate assay is then performed to get an approximate concentration of the DNA. Ligation reactions are then performed and 1 μl of the ligation reaction is packaged to construct a library. Packaging, for example, may occur through the use of purified λgt11 phage arms cut with EcoRI and DNA cut with EcoRI after attaching EcoRI linkers. The DNA and λgt11 arms are ligated with DNA ligase. The ligated DNA is then packaged into infectious phage particles. The packaged phages are used to infect *E. coli* cultures and the infected cells are spread on agar plates to yield plates carrying thousands of individual phage plaques. The library is then amplified.

Fragments of the full length gene of the present invention may be used as a hybridization probe for a cDNA or a genomic library to isolate the full length DNA and to isolate other DNAs which have a high sequence similarity to the gene or similar biological activity. Probes of this type have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons, and introns.

The isolated nucleic acid sequences and other enzymes may then be measured for retention of biological activity characteristic to the enzyme of the present invention, for example, in an assay for detecting enzymatic amidase activity. Such enzymes include truncated forms of amidase, and variants such as deletion and insertion variants.

The polynucleotide of the present invention may be in the form of DNA which DNA includes cDNA, genomic DNA, and synthetic DNA. The DNA may be double-stranded or single-stranded, and if single stranded may be the coding strand or non-coding (anti-sense) strand. The coding sequence which encodes the mature enzyme may be identical to the coding sequence shown in FIG. 1 (SEQ ID NO:1) and/or that of the deposited clone or may be a different coding sequence which coding sequence, as a result of the redundancy or degeneracy of the genetic code, encodes the same mature enzyme as the DNA of FIG. 1 (SEQ ID NO:1).

The polynucleotide which encodes for the mature enzyme of FIG. 1 (SEQ ID NO:2) may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence.

The present invention further relates to variants of the hereinabove described polynucleotides which encode for fragments, analogs and derivatives of the enzyme having the deduced amino acid sequence of FIG. 1 (SEQ ID NO:2). The variant of the polynucleotide may be a naturally occurring allelic variant of the polynucleotide or a non-naturally occurring variant of the polynucleotide.

Thus, the present invention includes polynucleotides encoding the same mature enzyme as shown in FIG. 1 (SEQ ID NO:2) as well as variants of such polynucleotides which variants encode for a fragment, derivative or analog of the enzyme of FIG. 1 (SEQ ID NO:2). Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1). As known in the art, an allelic variant is an alternate form of a polynucleotide sequence which may have a substitution, deletion or addition of one or more nucleotides, which does not substantially alter the function of the encoded enzyme.

The present invention also includes polynucleotides, wherein the coding sequence for the mature enzyme may be fused in the same reading frame to a polynucleotide sequence which aids in expression and secretion of an enzyme from a host cell, for example, a leader sequence which functions to control transport of an enzyme from the cell. The enzyme having a leader sequence is a preprotein and may have the leader sequence cleaved by the host cell to form the mature form of the enzyme. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature enzyme, or for an enzyme having a prosequence or for an enzyme having both a prosequence and a presequence (leader sequence).

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode enzymes which either retain substantially the same biological function or activity as the mature enzyme encoded by the DNA of FIG. 1 (SEQ ID NO:1).

Alternatively, the polynucleotide may have at least 15 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a PCR primer.

Thus, the present invention is directed to polynucleotides having at least a 70% identity, preferably at least 90% identity and more preferably at least a 95% identity to a polynucleotide which encodes the enzyme of SEQ ID NO:2 as well as fragments thereof, which fragments have at least 30 bases and preferably at least 50 bases and to enzymes encoded by such polynucleotides.

The present invention further relates to a enzyme which has the deduced amino acid sequence of FIG. 1 (SEQ ID NO:2), as well as fragments, analogs and derivatives of such enzyme.

The terms "fragment," "derivative" and "analog" when referring to the enzyme of FIG. 1 (SEQ ID NO:2) means a enzyme which retains essentially the same biological function or activity as such enzyme. Thus, an analog includes a proprotein which can be activated by cleavage of the proprotein portion to produce an active mature enzyme.

The enzyme of the present invention may be a recombinant enzyme, a natural enzyme or a synthetic enzyme, preferably a recombinant enzyme.

The fragment, derivative or analog of the enzyme of FIG. 1 (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzymes and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The enzymes of the present invention include the enzyme of SEQ ID NO:2 (in particular the mature enzyme) as well as enzymes which have at least 70% similarity (preferably at least 70% identity) to the enzyme of SEQ ID NO:2 and more preferably at least 90% similarity (more preferably at least 90% identity) to the enzyme of SEQ ID NO:2 and still more preferably at least 95% similarity (still more preferably at least 95% identity) to the enzyme of SEQ ID NO:2 and also include portions of such enzymes with such portion of the enzyme generally containing at least 30 amino acids and more preferably at least 50 amino acids.

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Center for Biological Information).

A variant, i.e. a "fragment", "analog" or "derivative" enzyme, and reference enzyme may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors containing the polynucleotides of this invention. Such vectors may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence (s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Bacillus subtilis; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II (Stratagene); pTRC99a, pKK223-3, pDR540, pRIT2T (Pharmacia); Eukaryotic: pXT1, pSG5 (Stratagene) pSVK3, pBPV, pMSG, pSVLSV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

The enzymes, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against the enzyme of the present invention may be used in screening for similar enzymes from other organisms and samples. Such screening techniques are known in the art, for example, one such screening assay is described in "Methods for Measuring Cellulase Activities", *Methods in Enzymology*, Vol 160, pp. 87–116, which is hereby incorporated by reference in its entirety. Antibodies may also be employed as a probe to screen gene libraries generated from this or other organisms to identify this or cross reactive activities.

The present invention is further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in the method of Sambrook, Fritsch and Maniatus, 1989.

EXAMPLE 1

Bacterial Expression and Purification of Amidase

A Thermococcus GU5L5 genomic library was screened for amidase activity as described in Example 2 and a positive clone was identified and isolated. DNA of this clone was used as a template in a 100 $\mu$l PCR reaction using the following primer sequences:

5' primer: CCGAGAATTC ATTAAAGAGG AGAAAT-TAAC TATGACCGGC ATCGAATGGA 3' (SEQ ID NO:3). 3' primer: 5' AATAAGGATC CACACTGGCA CAGTGTCAAG ACA 3' (SEQ ID NO:4).

The protein was expressed in *E. coli*. The gene was amplified using PCR with the primers indicated above.

Subsequent to amplification, the PCR product was cloned into the EcoRI and BamHI sites of pQET1 and transformed by electroporation into *E. coli* M15(pREP4). The resulting transformants were grown up in 3 ml cultures, and a portion of this culture was induced. A portion of the uninduced and induced cultures were assayed using Z-L-Phe-AMC (see below).

The primer sequences set out above may also be employed to isolate the target gene from the deposited material by hybridization techniques described above.

EXAMPLE 2

Discovery of an Amidase from Thermococcus GU5L5

Production of the Expression Gene Bank

Colonies containing pBluescript plasmids with random inserts from the organism Thermococcus GU5L5 was obtained according to the method of Hay and Short. (Hay, B. and Short, J., Strategies. 1992, 5, 16.) The resulting colonies were picked with sterile toothpicks and used to singly inoculate each of the wells of 96-well microtiter plates. The wells contained 250 μL of LB media with 100 μg/mL ampicillin, 80 μg/mL methicillin, and 10% v/v glycerol (LB Amp/Meth, glycerol). The cells were grown overnight at 37° C. without shaking. This constituted generation of the "SourceGeneBank"; each well of the Source GeneBank thus contained a stock culture of E. coli cells, each of which contained a pBluescript plasmid with a unique DNA insert.

Screening for Amidase Activity

The plates of the Source GeneBank were used to multiply inoculate a single plate (the "Condensed Plate") containing in each well 200 μL of LB Amp/Meth, glycerol. This step was performed using the High Density Replicating Tool (HDRT) of the Beckman Biomek with a 1% bleach, water, isopropanol, air-dry sterilization cycle in between each inoculation. Each well of the Condensed Plate thus contained 10 to 12 different pBluescript clones from each of the source library plates. The Condensed Plate was grown for 16 h at 37° C. and then used to inoculate two white 96-well Polyfiltronics microtiter daughter plates containing in each well 250 μL of LB Amp/Meth (without glycerol). The original condensed plate was put in storage –80° C. The two condensed daughter plates were incubated at 37° C. for 18 h.

The '600 μM substrate stock solution' was prepared as follows: 25 mg of N-morphourea-L-phenylalanyl-7-amido-4-trifluoromethylcoumarin(Mu-Phe-AFC, EnzymeSystems Products, Dublin, Calif.) was dissolved in the appropriate volume of DMSO to yield a 25.2 mM solution. Two hundred fifty microliters of DMSO solution was added to ca. 9 mL of 50 mM, pH 7.5 Hepes buffer containing 0.6 mg/mL of dodecyl maltoside. The volume was taken to 10.5 mL with the above Hepes buffer to yield a cloudy solution.

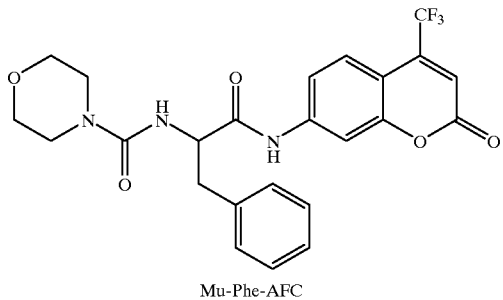

Mu-Phe-AFC

Fifty μL of the '600 μM stock solution' was added to each of the wells of a white condensed plate using the Biomek to yield a final concentration of substrate of ~100 μM. The fluorescence values were recorded (excitation=400 nm, emission=505 nm) on a plate reading fluorometer immediately after addition of the substrate. The plate was incubated at 70° C. for 60 min. and the fluorescence values were recorded again. The initial and final fluorescence values were subtracted to determine if an active clone was present by an increase in fluorescence over the majority of the other wells.

Isolation of the Active Clone

In order to isolate the individual clone which carried the activity, the Source GeneBank plates were thawed and the individual wells used to singly inoculate a new plate containing LB Amp/Meth. As above the plate was incubated at 37° C. to grow the cells, and 50 μL of 600 μM substrate stock solution added using the Biomek. Once the active well from the source plate was identified, the cells from the source plate were used to inoculate 3 mL cultures of LB/AMP/Meth, which were grown overnight. The plasmid DNA was isolated from the cultures and utilized for sequencing and construction of expression subclones.

EXAMPLE 3

Thermococcus GU5L5 Amidase Characterization

Substrate Specificity

Using the following substrates (see below for definitions of the abbreviations): CBZ-L-ala-AMC, CBZ-L-arg-AMC, CBZ-L-met-AMC, CBZ-L-phe-AMC, and 7-methyl-umbelliferyl heptanoate at 100 μM for 1 hour at 70° C. in the assays as described in the clone discovery section, the relative activity of the amidase was 3:3:1:<0.1:<0.1 for the compounds CBZ-L-arg-AMC: CBZ-L-phe-AMC: CBZ-L-met-AMC: CBZ-L-ala-AMC : 7-methylumbelliferyl heptanoate. The excitation and emission wavelengths for the 7-amido-4-methylcoumarins were 380 and 460 nm respectively, and 326 and 450 for the methylumbelliferone.

The abbreviations stand for the following compounds:

CBZ-L-ala-AMC=Nα-carbonylbenzyloxy-L-alanine-7-amido-4-methylcoumarin

CBZ-L-arg-AMC=Nα-carbonylbenzyloxy-L-arginine-7-amido-4-methylcoumarin

CBZ-D-arg-AMC=Nα-carbonylbenzyloxy-D-arginine-7-amido-4-methylcoumarin

CBZ-L-met-AMC=Nα-carbonylbenzyloxy-L-methionine-7-amido-4-methylcoumarin

CBZ-L-phe-AMC=Nα-carbonylbenzyloxy-L-phenylalanine-7-amido-4-methylcoumarin

Organic Solvent Sensitivity

The activity of the amidase in increasing concentrations of dimethyl sulfoxide (DMSO) was tested as follows: to each well of a microtiter plate was added 10 μL of 3 mM CBZ-L-phe-AMC in DMSO, 25 μL of cell lysate containing the amidase activity, and 250 μL of a variable mixture of DMSO:pH 7.5, 50 mM Hepes buffer. The reactions were heated for 1 hour at 70° C. and the fluorescence measured. FIG. 2 shows the fluorescence versus concentration of DMSO. The filled and open boxes represent individual assays.

Figure 3:
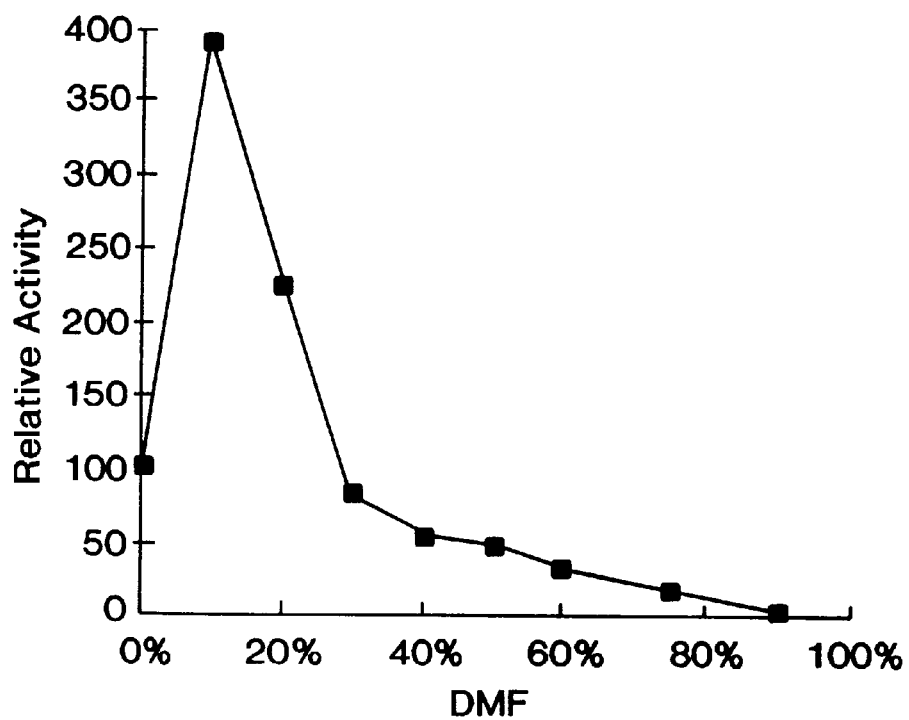
FIG. 3 shows the relative initial linear rates (increase in fluorescence per min. i.e. "activity") versus concentration of DMF for the more reactive CBZ-L-arg-AMC, from Example 3.

The activity and enantioselectivity of the amidase in increasing concentrations of dimethyl formamide (DMF) was tested as follows: to each well of a microtiter plate was added 30 μL of 1 mM CBZ-L-arg-AMC or CBZ-D-arg-AMC in DMF, 30 μL of cell lysate containing the amidase activity, and 240 μL of a variable mixture of DMF:pH 7.5, 50 mM Hepes buffer. The reactiosn were incubated at RT for 1 hour and the fluorescence measured at 1 minute intervals. FIG. 3 shows the relative initial linear rates (increase in fluorescence per min, i.e., 'activity') versus concentration of DMF for the more reactive CBZ-L-arg-AMC.

The initial linear rate ('activity') of the L and the D CBZ-arg-AMC substrates are shown in Tables 1 and 2 below:

TABLE 1

Activity of the CBZ-L-arg-AMC

| DMF | Initial Rate, Fl.U./min |
|---|---|
| 0.4% | 654 |
| 10% | 2548 |
| 20% | 1451 |
| 30% | 541 |
| 40% | 345 |
| 50% | 303 |
| 60% | 190 |
| 75% | 81 |
| 90% | 11 |

TABLE 2

Activity of the CBZ-D-arg-AMC

| DMF | Initial Rate, Fl.U./min |
|---|---|
| 0.4% | 0.3 |
| 10% | 10.1 |
| 20% | 4.6 |
| 30% | 1.8 |
| 40% | 0.9 |
| 50% | 1.2 |
| 60% | 1.4 |
| 75% | 0.1 |
| 90% | 0.1 |

The above data indicate that the enzyme shows excellent selectivity for the L, or 'natural' enantiomer of the derivatized amino acid substrate.

Numerous modifications and variations of the present invention are possible in light of the above teachings and, therefore, within the scope of the appended claims, the invention may be practiced otherwise than as particularly described.

What is claimed is:

1. A purified variant protein of SEQ ID NO: 2 which is at least 70% identical, but not 100% identical to SEQ ID NO: 2 and which catalyze removal of arginine, phenylalanine or methionine from the N-terminal end of peptides in peptide or peptidomimetic synthesis.

2. The purified protein of claim 1, wherein the variants are at least about 90% identical to SEQ ID NO:2.

3. The purified protein of claim 1, wherein the variants are at least about 95% identical to SEQ ID NO:2.

4. The purified protein of claim 1, which comprises at least 30 contiguous amino acid residues.

5. A method for removal of arginine, phenylalanine or methionine from the N-terminal end of peptides in peptide or peptidomimetic synthesis, comprising:
    contacting the peptides with an amount of an enzyme of claim 1 effective for removal of arginine, phenylalanine or methionine from the N-terminal end of peptides in peptide or peptidomimetic synthesis.

* * * * *

SEQUENCE LISTING (1) GENERAL INFORMATION:

(iii) NUMBER OF SEQUENCES:  4

(2) INFORMATION FOR SEQ ID NO:1:

(i) SEQUENCE CHARACTERISTICS:
      (A) LENGTH:  1869 NUCLEOTIDES (B) TYPE:  NUCLEIC ACID (C) STRANDEDNESS:  SINGLE (D) TOPOLOGY:  LINEAR (ii) MOLECULE TYPE:  DNA (xi) SEQUENCE DESCRIPTION:  SEQ ID NO:1:

```
ATG ACC GGC ATC GAA TGG AAC CAC GAG ACC TTT TCT AAG TTC GCC TAC        48
Met Thr Tly Ile Glu Trp Asn His Glu Thr Phe Ser Lys Phe Ala Tyr
5                   10                  15

CTG GGC GAC CCG AGG ATA CGG GGA AAC TTA ATC GCG TAC ACC CTG ACG        96
Leu Gly Asp Pro Arg Ile Arg Gly Asn Leu Ile Ala Tyr Thr Leu Thr
20                  25                  30

AAG GCC AAC ATG AAG GAC AAC AAG TAC GAG AGC ACG GTT GTT GTT GAA       144
Lys Ala Asn Met Lys Asp Asn Lys Tyr Glu Ser Thr Val Val Val Glu
35                  40                  45

GAC CTT GAA ACG GGC TCA AGG CGC TTC ATC GAG AAC GCC TCA ATG CCG       192
Asp Leu Glu Thr Gly Ser Arg Arg Phe Ile Glu Asn Ala Ser Met Pro
50                  55                  60

AGG ATT TCG CCA GAC GGC AGA AAG CTC GCC TTC ACC TGC TTT AAC GAG       240
Arg Ile Ser Pro Asp Gly Arg Lys Leu Ala Phe Thr Cys Phe Asn Glu
65                  70                  75                  80

GAG AAG AAG GAG ACC GAG ATA TGG GTG GCC GAT ATC CAG ACC CTG AGC       288
Glu Lys Lys Glu Thr Glu Ile Trp Val Ala Asp Ile Gln Thr Leu Ser
85                  90                  95

GCC AAG AAA GTC CTC TCA ACT AAA AAC GTC CGC TCG ATG CAG TGG AAC       336
Ala Lys Lys Val Leu Ser Thr Lys Asn Val Arg Ser Met Gln Trp Asn
```

```
                                                      -continued
100                     105                     110

GAC GAT TCA AGG AGA CTC TTA GTT GTC GGC TTC AAG AGG AGG GAC GAT          384
Asp Asp Ser Arg Arg Leu Leu Val Val Gly Phe Lys Arg Arg Asp Asp
115                     120                     125

GAG GAC TTC GTC TTT GAC GAC GAC GTC CCG GTC TGG TTC GAC AAT ATG          432
Glu Asp Phe Val Phe Asp Asp Asp Val Pro Val Trp Phe Asp Asn Met
130                     135                     140

GGA TTC TTT GAT GGA GAG AAG ACG ACG TTC TGG GTT CTT GAC ACT GAG          480
Gly Phe Phe Asp Gly Glu Lys Thr Thr Phe Trp Val Leu Asp Thr Glu
145                     150                     155                 160

GCC GAG GAG ATA ATC GAG CAG TTC GAG AAG CCG AGG TTT TCG AGT GGC          528
Ala Glu Glu Ile Ile Glu Gln Phe Glu Lys Pro Arg Phe Ser Ser Gly
165                     170                     175

CTC TGG CAC GGC GAT GCG ATA GTT GTG AAC GTC CCG CAC CGC GAG GGG          576
Leu Trp His Gly Asp Ala Ile Val Val Asn Val Pro His Arg Glu Gly
180                     185                     190

AGC AAG CCT GCC CTG TTC AAG TTC TAC GAC ATA GTC CTA TGG AAG GAC          624
Ser Lys Pro Ala Leu Phe Lys Phe Tyr Asp Ile Val Leu Trp Lys Asp
195                     200                     205

GGG GAG GAA GAG AAG CTC TTC GAG AGG GTC TCC TTC GAG GCG GTT GAC          672
Gly Glu Glu Glu Lys Leu Phe Glu Arg Val Ser Phe Glu Ala Val Asp
210                     215                     220

TCC GAC GGA AAG AGA ATA CTC CTG AGG GGC AAG AAA AAA AAG CGG TTC          720
Ser Asp Gly Lys Arg Ile Leu Leu Arg Gly Lys Lys Lys Lys Arg Phe
225                     230                     235                 240

ATC AGC GAG CAC GAC TGG CTG TAC CTC TGG GAC GGC GAG CTT AAA CCG          768
Ile Ser Glu His Asp Trp Leu Tyr Leu Trp Asp Gly Glu Leu Lys Pro
245                     250                     255

ATC TAC GAG GGC CCG CTC GAC GTC TGG GAA GCC AAG CTC ACG GAA GGA          816
Ile Tyr Glu Gly Pro Leu Asp Val Trp Glu Ala Lys Leu Thr Glu Gly
260                     265                     270

AAG GTC TAC TTC CTC ACT CCA GAT GCG GGC AGG GTA AAC CTC TGG CTC          864
Lys Val Tyr Phe Leu Thr Pro Asp Ala Gly Arg Val Asn Leu Trp Leu
275                     280                     285

TGG GAC GGG AAG GCC GAG CGT GTT GTT ACC GGC GAC CAC TGG ATT TAC          912
Trp Asp Gly Lys Ala Glu Arg Val Val Thr Gly Asp His Trp Ile Tyr
290                     295                     300

GGG CTT GAC GTC AGC GAT GGC AAA GCA TTG CTC CTC ATC ATG ACC GCC          960
Gly Leu Asp Val Ser Asp Gly Lys Ala Leu Leu Leu Ile Met Thr Ala
305                     310                     315                 320

ACG AGG ATA GGC GAG CTC TAC CTC TAC GAC GGC GAG CTG AAA CAG GTC         1008
Thr Arg Ile Gly Glu Leu Tyr Leu Tyr Asp Gly Glu Leu Lys Gln Val
325                     330                     335

ACC GAA TAC AAC GGG CCG ATA TTC AGG AAG CTC AAG ACC TTC GAG CCG         1056
Thr Glu Tyr Asn Gly Pro Ile Phe Arg Lys Leu Lys Thr Phe Glu Pro
340                     345                     350

AGG CAC TTC CGC TTC AAG AGC AAA GAC CTC GAG ATA GAC GGC TGG TAC         1104
Arg His Phe Arg Phe Lys Ser Lys Asp Leu Glu Ile Asp Gly Trp Tyr
355                     360                     365

CTC AGG CCG GAG GTT AAA GAG GAG AAG GCC CCG GTG ATA GTC TTC GTC         1152
Leu Arg Pro Glu Val Lys Glu Glu Lys Ala Pro Val Ile Val Phe Val
370                     375                     380

CAC GGC GGG CCG AAG GGC ATG TAC GGA CAC CGC TTC GTC TAC GAG ATG         1200
His Gly Gly Pro Lys Gly Met Tyr Gly His Arg Phe Val Tyr Glu Met
385                     390                     395                 400

CAG CTG ATG GCG AGC AAG GGC TAC TAC TGC TGC TTC GTG AAC CCG CGC         1248
Gln Leu Met Ala Ser Lys Gly Tyr Tyr Cys Cys Phe Val Asn Pro Arg
405                     410                     415

GGC AGC GAC GGC TAT AGC GAA GAC TTC GCG CTC CGC GTC CTG GAG AGG         1296
```

```
            Gly Ser Asp Gly Tyr Ser Glu Asp Phe Ala Leu Arg Val Leu Glu Arg
            420                 425                 430

ACT GGC TTG GAG GAC TTT GAG GAC ATA ATG AAC GGC ATC GAG GAG TTC         1344
Thr Gly Leu Glu Asp Phe Glu Asp Ile Met Asn Gly Ile Glu Glu Phe
435                 440                 445

TTC AAG CTC GAA CCG CAG GCC GAC AGG GAG CGC GTT GGA ATA ACG GGC         1392
Phe Lys Leu Glu Pro Gln Ala Asp Arg Glu Arg Val Gly Ile Thr Gly
450                 455                 460

ATA AGC TAC GGC GGC TTC ATG ACC AAC TGG GCC TTG ACT CAG AGC GAC         1440
Ile Ser Tyr Gly Gly Phe Met Thr Asn Trp Ala Leu Thr Gln Ser Asp
465                 470                 475                 480

CTC TTC AAG GCA GGA ATA AGC GAG AAC GGC ATA AGC TAC TGG CTC ACC         1488
Leu Phe Lys Ala Gly Ile Ser Glu Asn Gly Ile Ser Tyr Trp Leu Thr
485                 490                 495

AGC TAC GCC TTC TCG GAC ATA GGG CTC TGG TAC GAC GTC GAG GTC ATC         1536
Ser Tyr Ala Phe Ser Asp Ile Gly Leu Trp Tyr Asp Val Glu Val Ile
500                 505                 510

GGG CCA AAT CCG TTA GAG AAC GAG AAC TTC AGG AAG CTC AGC CCG CTG         1584
Gly Pro Asn Pro Leu Glu Asn Glu Asn Phe Arg Lys Leu Ser Pro Leu
515                 520                 525

TTC TAC GCT CAG AAC GTG AAG GCG CCG ATA CTC CTA ATC CAC TCG CTT         1632
Phe Tyr Ala Gln Asn Val Lys Ala Pro Ile Leu Leu Ile His Ser Leu
530                 535                 540

GAG GAC TAC CGC TGT CCG CTC GAC CAG AGC CTT ATG TTC TAC AAC GTG         1680
Glu Asp Tyr Arg Cys Pro Leu Asp Gln Ser Leu Met Phe Tyr Asn Val
545                 550                 555                 560

CTC AAG GAC ATG GGC AAG GAA GCC TAC ATA GCG ATA TTC AAG CGC GGC         1728
Leu Lys Asp Met Gly Lys Glu Ala Tyr Ile Ala Ile Phe Lys Arg Gly
565                 570                 575

GCC CAC GGC CAC AGC GTC CGC GGA AGC CCG AGG CAC AGG CCG AAG CGC         1776
Ala His Gly His Ser Val Arg Gly Ser Pro Arg His Arg Pro Lys Arg
580                 585                 590

TAC AGG CTC TTC ATA GAG TTC TTC GAG CGC AAG CTC AAG AAG TAC GAG         1824
Tyr Arg Leu Phe Ile Glu Phe Phe Glu Arg Lys Leu Lys Lys Tyr Glu
595                 600                 605

GAG GGC TTT GAG GTA GAG AAG ATA CTC AAG GGG AAT GGG AAC TGA             1869
Glu Gly Phe Glu Val Glu Lys Ile Leu Lys Gly Asn Gly Asn
610                 615                 620

(2) INFORMATION FOR SEQ ID NO:2:

(i) SEQUENCE CHARACTERISTICS:
        (A) LENGTH: 622 AMINO ACIDS (B) TYPE: AMINO ACID (C) STRANDEDNESS:

(D) TOPOLOGY: LINEAR (ii) MOLECULE TYPE: PROTEIN (xi) SEQUENCE DESCRIPTION: SEQ ID NO:2:

Met Thr Gly Ile Glu Trp Asn His Glu Thr Phe Ser Lys Phe Ala Tyr
                5                  10                  15

Leu Gly Asp Pro Arg Ile Arg Gly Asn Leu Ile Ala Tyr Thr Leu Thr
            20                  25                  30

Lys Ala Asn Met Lys Asp Asn Lys Tyr Glu Ser Thr Val Val Val Glu
        35                  40                  45

Asp Leu Glu Thr Gly Ser Arg Arg Phe Ile Glu Asn Ala Ser Met Pro
50                  55                  60
```

```
Arg Ile Ser Pro Asp Gly Arg Lys Leu Ala Phe Thr Cys Phe Asn Glu
 65                  70                  75                  80

Glu Lys Lys Glu Thr Glu Ile Trp Val Ala Asp Ile Gln Thr Leu Ser
                 85                  90                  95

Ala Lys Lys Val Leu Ser Thr Lys Asn Val Arg Ser Met Gln Trp Asn
            100                 105                 110

Asp Asp Ser Arg Arg Leu Leu Val Gly Phe Lys Arg Arg Asp Asp
            115                 120                 125

Glu Asp Phe Val Phe Asp Asp Val Pro Val Trp Phe Asp Asn Met
130                 135                 140

Gly Phe Phe Asp Gly Glu Lys Thr Thr Phe Trp Val Leu Asp Thr Glu
145                 150                 155                 160

Ala Glu Glu Ile Ile Glu Gln Phe Glu Lys Pro Arg Phe Ser Ser Gly
                165                 170                 175

Leu Trp His Gly Asp Ala Ile Val Val Asn Val Pro His Arg Glu Gly
            180                 185                 190

Ser Lys Pro Ala Leu Phe Lys Phe Tyr Asp Ile Val Leu Trp Lys Asp
            195                 200                 205

Gly Glu Glu Glu Lys Leu Phe Glu Arg Val Ser Phe Glu Ala Val Asp
            210                 215                 220

Ser Asp Gly Lys Arg Ile Leu Leu Arg Gly Lys Lys Lys Arg Phe
225                 230                 235                 240

Ile Ser Glu His Asp Trp Leu Tyr Leu Trp Asp Gly Glu Leu Lys Pro
                245                 250                 255

Ile Tyr Glu Gly Pro Leu Asp Val Trp Glu Ala Lys Leu Thr Glu Gly
            260                 265                 270

Lys Val Tyr Phe Leu Thr Pro Asp Ala Gly Arg Val Asn Leu Trp Leu
            275                 280                 285

Trp Asp Gly Lys Ala Glu Arg Val Val Thr Gly Asp His Trp Ile Tyr
290                 295                 300

Gly Leu Asp Val Ser Asp Gly Lys Ala Leu Leu Leu Ile Met Thr Ala
305                 310                 315                 320

Thr Arg Ile Gly Glu Leu Tyr Leu Tyr Asp Gly Glu Leu Lys Gln Val
                325                 330                 335

Thr Glu Tyr Asn Gly Pro Ile Phe Arg Lys Leu Lys Thr Phe Glu Pro
                340                 345                 350

Arg His Phe Arg Phe Lys Ser Lys Asp Leu Glu Ile Asp Gly Trp Tyr
                355                 360                 365

Leu Arg Pro Glu Val Lys Glu Glu Lys Ala Pro Val Ile Val Phe Val
370                 375                 380

His Gly Gly Pro Lys Gly Met Tyr Gly His Arg Phe Val Tyr Glu Met
385                 390                 395                 400

Gln Leu Met Ala Ser Lys Gly Tyr Tyr Val Phe Val Asn Pro Arg
                405                 410                 415

Gly Ser Asp Gly Tyr Ser Glu Asp Phe Ala Leu Arg Val Leu Glu Arg
            420                 425                 430

Thr Gly Leu Glu Asp Phe Glu Asp Ile Met Asn Gly Ile Glu Glu Phe
            435                 440                 445

Phe Lys Leu Glu Pro Gln Ala Asp Arg Glu Arg Val Gly Ile Thr Gly
            450                 455                 460

Ile Ser Tyr Gly Gly Phe Met Thr Asn Trp Ala Leu Thr Gln Ser Asp
465                 470                 475                 480
```

```
Leu Phe Lys Ala Gly Ile Ser Glu Asn Gly Ile Ser Tyr Trp Leu Thr
            485                 490                 495

Ser Tyr Ala Phe Ser Asp Ile Gly Leu Trp Tyr Asp Val Glu Val Ile
            500                 505                 510

Gly Pro Asn Pro Leu Glu Asn Glu Asn Phe Arg Lys Leu Ser Pro Leu
            515                 520                 525

Phe Tyr Ala Gln Asn Val Lys Ala Pro Ile Leu Leu Ile His Ser Leu
            530                 535                 540

Glu Asp Tyr Arg Cys Pro Leu Asp Gln Ser Leu Met Phe Tyr Asn Val
545                 550                 555                 560

Leu Lys Asp Met Gly Lys Glu Ala Tyr Ile Ala Ile Phe Lys Arg Gly
                565                 570                 575

Ala His Gly His Ser Val Arg Gly Ser Pro Arg His Arg Pro Lys Arg
                580                 585                 590

Tyr Arg Leu Phe Ile Glu Phe Phe Glu Arg Lys Leu Lys Lys Tyr Glu
            595                 600                 605

Glu Gly Phe Glu Val Glu Lys Ile Leu Lys Gly Asn Gly Asn
            610                 615                 620
```

(2) INFORMATION FOR SEQ ID NO:3:

(i) SEQUENCE CHARACTERISTICS:
        (A) LENGTH: 50 NUCLEOTIDES (B) TYPE: NUCLEIC ACID (C) STRANDEDNESS: SINGLE (D) TOPOLOGY: LINEAR (ii) MOLECULE TYPE: Oligonucleotide (xi) SEQUENCE DESCRIPTION: SEQ ID NO:3:

```
CCGAGAATTC ATTAAAGAGG AGAAATTAAC TATGACCGGC ATCGAATGGA          50
```

(2) INFORMATION FOR SEQ ID NO:4:

(i) SEQUENCE CHARACTERISTICS:
        (A) LENGTH: 33 NUCLEOTIDES (B) TYPE: NUCLEIC ACID (C) STRANDEDNESS: SINGLE (D) TOPOLOGY: LINEAR (ii) MOLECULE TYPE: Oligonucleotide (xi) SEQUENCE DESCRIPTION: SEQ ID NO:4:

```
AATAAGGATC CACACTGGCA CAGTGTCAAG ACA                            33
```